United States Patent
Worthen (10) Patent No.: US 10,968,795 B2
(45) Date of Patent: Apr. 6, 2021

(54) METHODS AND SYSTEMS FOR DETECTION OF PARTICLES IN LUBRICANT

(71) Applicant: Ford Global Technologies, LLC, Dearborn, MI (US)

(72) Inventor: Reid Worthen, Dearborn, MI (US)

(73) Assignee: Ford Global Technologies, LLC, Dearborn, MI (US)

(*) Notice: Subject to any disclaimer, the term of this patent is extended or adjusted under 35 U.S.C. 154(b) by 49 days.

(21) Appl. No.: 16/379,592

(22) Filed: Apr. 9, 2019

(65) Prior Publication Data
US 2020/0325806 A1    Oct. 15, 2020

(51) Int. Cl.
| | | |
|---|---|---|
| *F01M 11/00* | (2006.01) | |
| *F01M 11/10* | (2006.01) | |
| *G01N 33/28* | (2006.01) | |
| *F01M 11/03* | (2006.01) | |
| *F02P 5/15* | (2006.01) | |
| *F02P 5/04* | (2006.01) | |
| *F02D 41/30* | (2006.01) | |
| *F01M 11/02* | (2006.01) | |

(52) U.S. Cl.
CPC .......... *F01M 11/10* (2013.01); *F01M 11/02* (2013.01); *F01M 11/03* (2013.01); *F02D 41/3005* (2013.01); *F02P 5/045* (2013.01); *F02P 5/15* (2013.01); *G01N 33/2858* (2013.01); *G01N 33/2888* (2013.01); *F01M 2011/144* (2013.01); *F01M 2011/1466* (2013.01)

(58) Field of Classification Search
CPC ........ F01M 11/10; F01M 11/02; F01M 11/03; F01M 2011/1466; F02P 5/15; F02P 5/045; G01N 33/2858; G01N 33/2888; F02D 41/3005
See application file for complete search history.

(56) References Cited

U.S. PATENT DOCUMENTS

| | | | | |
|---|---|---|---|---|
| 1,778,910 A | * | 10/1930 | MacPhail | B01D 35/005 210/223 |
| 3,342,339 A | * | 9/1967 | Riolo | B01D 27/08 210/223 |
| 4,675,662 A | * | 6/1987 | Kondo | G01N 17/00 324/698 |
| 4,795,903 A | * | 1/1989 | Clayton | G01N 23/222 250/301 |
| 5,402,113 A | * | 3/1995 | Naas | G01N 15/0656 200/61.09 |
| 5,674,401 A | | 10/1997 | Dickert et al. | |

(Continued)

FOREIGN PATENT DOCUMENTS

EP    1521081 A1    4/2005
EP    2455774 A1    5/2012

*Primary Examiner* — Phutthiwat Wongwian
*Assistant Examiner* — Sherman D Manley
(74) *Attorney, Agent, or Firm* — Geoffrey Brumbaugh; McCoy Russell LLP (57) ABSTRACT

Methods and systems are provided for a lubricant detection device. In one example, a system comprises one or more sensors arranged in an oil flow path for detecting if a particle is in an oil flow. Engine operating parameters are adjusted in response to sensing the particle, wherein the engine operating parameter adjustments are different in response to only a first sensor detecting the particle or to both the first sensor and a second sensor detecting the particle.

14 Claims, 8 Drawing Sheets

(56) References Cited

U.S. PATENT DOCUMENTS

| | | | | |
|---|---|---|---|---|
| 5,968,371 A * | 10/1999 | Verdegan | | F01M 1/16 |
| | | | | 184/108 |
| 5,982,847 A * | 11/1999 | Nelson | | G01N 33/2858 |
| | | | | 378/45 |
| 6,009,760 A * | 1/2000 | Jakkula | | G01F 1/712 |
| | | | | 73/861.05 |
| 6,151,108 A * | 11/2000 | Kwon | | G01N 21/534 |
| | | | | 356/70 |
| 6,196,058 B1 * | 3/2001 | Chen | | G01N 11/08 |
| | | | | 73/54.04 |
| 6,216,528 B1 * | 4/2001 | Carrell | | F02M 57/025 |
| | | | | 73/54.01 |
| 6,304,176 B1 * | 10/2001 | Discenzo | | G01H 1/003 |
| | | | | 340/506 |
| 6,508,107 B2 * | 1/2003 | Carrell | | F02D 41/3809 |
| | | | | 123/381 |
| 6,561,010 B2 * | 5/2003 | Wilson | | G01N 33/2888 |
| | | | | 73/54.04 |
| 6,675,635 B2 * | 1/2004 | Kasen | | G01N 33/2888 |
| | | | | 73/53.05 |
| 7,078,909 B2 * | 7/2006 | Feng | | G01N 27/023 |
| | | | | 324/127 |
| 7,321,117 B2 | 1/2008 | Liu | | |
| 7,581,434 B1 * | 9/2009 | Discenzo | | G01N 33/2888 |
| | | | | 73/53.01 |
| 7,832,257 B2 * | 11/2010 | Weightman | | G01N 11/04 |
| | | | | 73/54.09 |
| 8,368,894 B2 * | 2/2013 | Stevens | | G01N 21/05 |
| | | | | 356/436 |
| 8,897,953 B2 * | 11/2014 | Olsen, III | | G07C 5/02 |
| | | | | 701/31.6 |
| 9,581,433 B2 * | 2/2017 | Tixier | | G01B 9/02001 |
| 2002/0011095 A1 * | 1/2002 | Park | | G01N 27/221 |
| | | | | 73/54.01 |
| 2002/0140564 A1 * | 10/2002 | Danyluk | | G01N 27/002 |
| | | | | 340/603 |
| 2007/0063140 A1 * | 3/2007 | Liu | | G01N 15/0205 |
| | | | | 250/301 |
| 2008/0143351 A1 * | 6/2008 | Lee | | G01N 27/07 |
| | | | | 324/698 |
| 2009/0185188 A1 | 7/2009 | Verdegan et al. | | |
| 2009/0240471 A1 * | 9/2009 | Novis | | G05B 23/0229 |
| | | | | 702/183 |
| 2013/0330205 A1 * | 12/2013 | Apostolides | | F04B 23/04 |
| | | | | 417/12 |
| 2015/0075268 A1 | 3/2015 | Qi | | |
| 2017/0081997 A1 * | 3/2017 | Potyrailo | | G01N 27/026 |
| 2019/0156600 A1 * | 5/2019 | Potyrailo | | B61C 17/08 |

* cited by examiner

METHODS AND SYSTEMS FOR DETECTION OF PARTICLES IN LUBRICANT

FIELD

The present description relates generally to detecting foreign particles in lubricant and adjusting engine operating parameters in response to the detecting.

BACKGROUND/SUMMARY

Lubricants, such as oil, are used to lubricate various moving parts of a vehicle, including the engine and transmission. Foreign particles may enter the oil due to ageing of vehicle components or lack of lubrication thereof as some examples. An oil filter may be shaped to capture these particles and block their flow to engine and transmission components.

After a duration of time, it may be desired to replace the oil and the oil filter. However, this may be cumbersome for some vehicle operators and the oil and oil filter may be replaced less often than desired. In such instances, the oil filter may become filled with particles, such that oil flow is adversely affected or particles may no longer be captured by the filter.

Other examples of addressing degraded oil and/or oil filters include arranging sensors in an oil flow path to detect large particles. One example approach is shown by Liu in U.S. Pat. No. 7,321,117. Therein, a plurality of photo-detectors and a plurality of light-emitting devices are arranged in an oil flow path. A portion of the photo-detectors and the light-emitting devices may be sensitive to small-particles and a remaining portion may be sensitive to large-particles. However, the inventors have identified some issues with this approach.

For example, vehicle operators prone to extending use of the oil and the oil filter beyond its replacement date may also be prone to ignoring feedback regarding particles in the oil. Additionally, arrangement of the photo-detectors and the light-emitting devices may be difficult during a manufacturing process, resulting in an increased manufacturing costs and replacement costs.

In one example, the issues described above may be at least partially addressed by a system comprising a lubricant passage comprising a particle capturing device arranged between a first sensor and a second sensor. The system further comprising a controller with instructions stored on non-transitory memory thereof that when executed enable the controller to adjust engine operating parameters in response to feedback from the first and second sensors. In this way, if particles are detected in the oil, engine operating parameters may be adjusted to mitigate degradation to lubricated components during the time between the detection and the oil being replaced.

As one example, the engine operating parameters are adjusted to activate an indicator lamp in response to one or more particles being detected in a lubricant flow. As such, the vehicle operator may be notified of the at least one particle and able to replace the lubricant before the particle is able to reach the engine. The instructions may further enable the controller to adjust engine operating parameters to decrease an engine power output in response to the second sensor detecting particles in the lubricant flow. In such a condition, the particle is detected by the first sensor, and flows around or through the particle capturing device and past the second sensor, where the particle may reach moving engine, transmission, or other powertrain components. The second sensor may detect the particle if the vehicle operator does not replace the oil, if an oil filter is degraded, and/or if a powertrain component is degraded. By decreasing the engine power output, degradation caused by the particle may be mitigated.

It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

DETAILED DESCRIPTION

Figure 1:
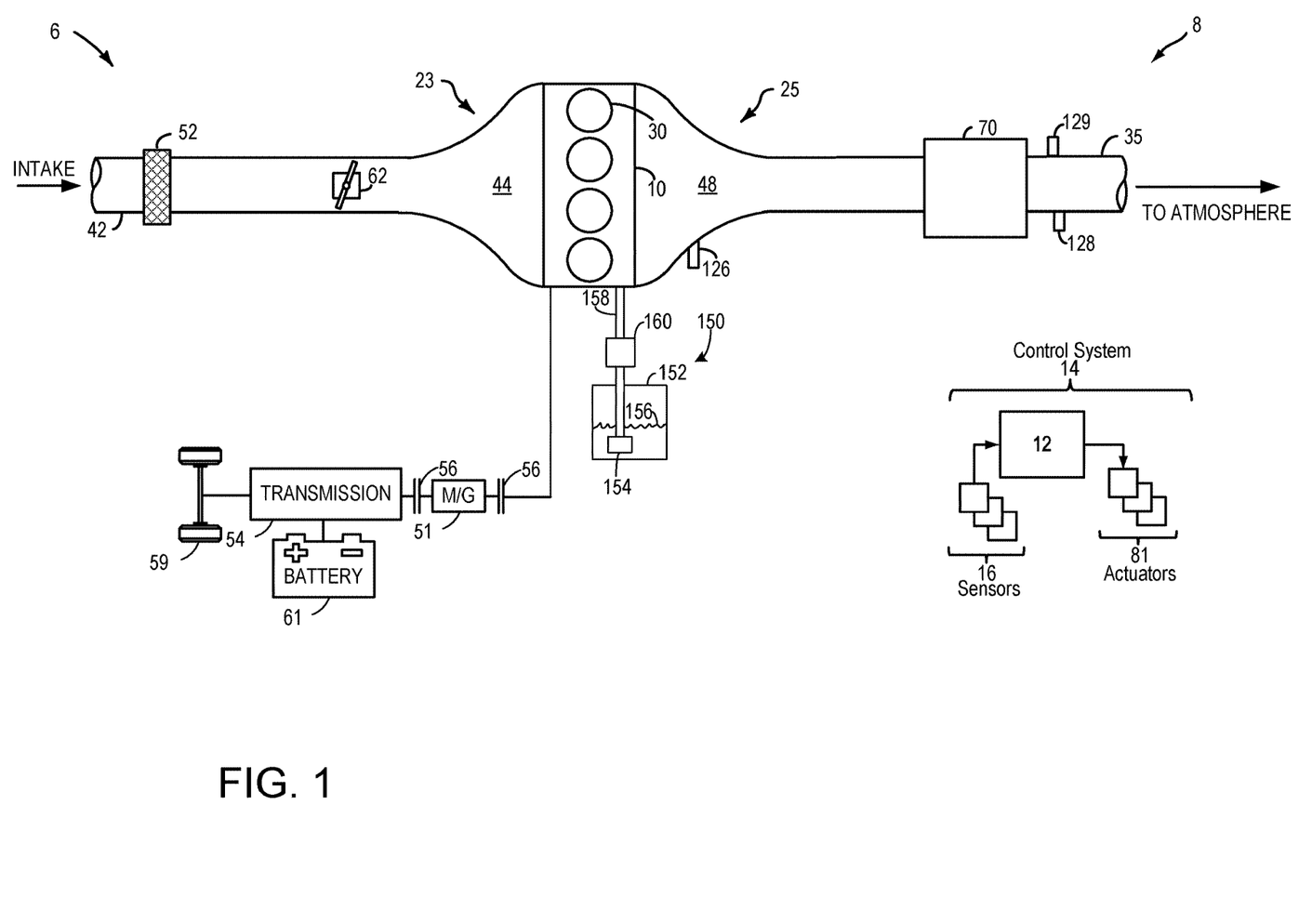
FIG. 1 illustrates a schematic of an engine included in a hybrid vehicle.
Figure 2:
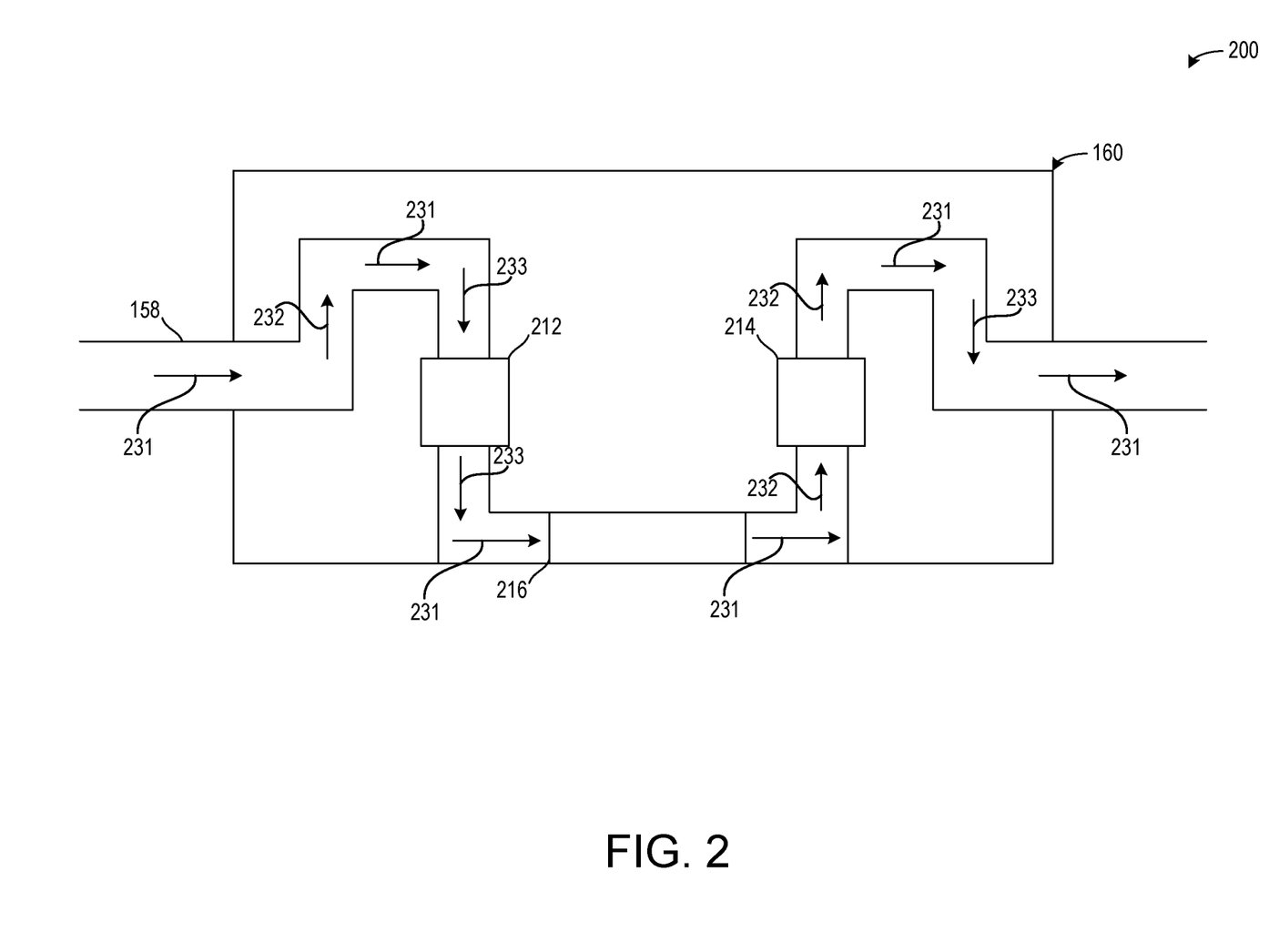
FIG. 2 illustrates a first example of a detection device.

The following description relates to systems and methods for detecting a particle in the oil. The particle may be detected via a detection device, such as a lubricant detection device, that may be arranged along an oil path from an oil pan to an engine. FIG. 1 shows an example of the lubricant detection device arranged between an oil sump and the engine. A first example of the lubricant detection device is shown in FIG. 2. Therein, the lubricant detection device comprises a first second and a second sensor with a particle capturing device arranged therebetween.

Figure 3:
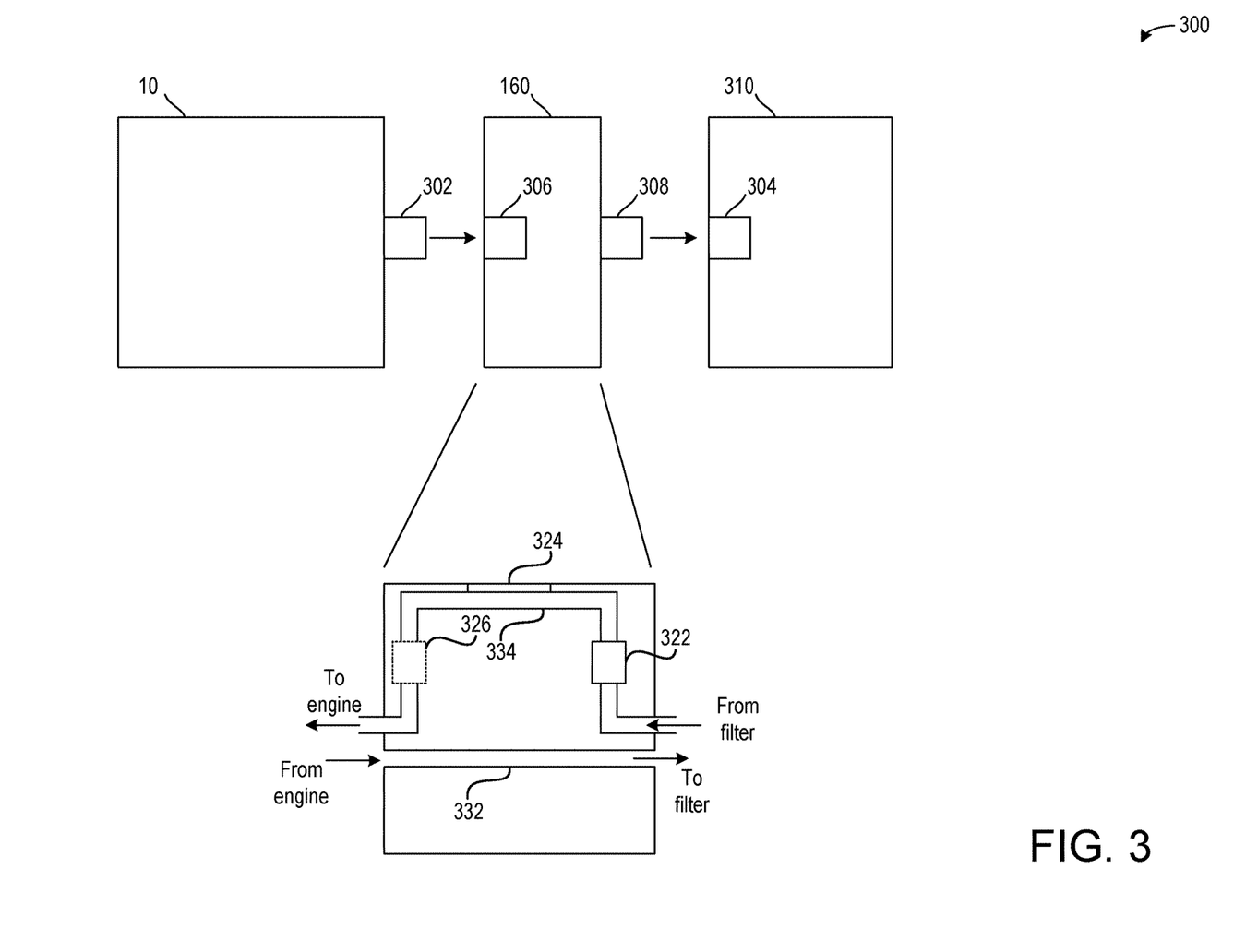
FIG. 3 illustrates a second example of a detection device.

A second example of the lubricant detection device is shown in FIG. 3. Therein, the second example comprises one or more couplings shaped to mate with couplings corresponding to an engine and an oil filter so that the lubricant detection device may be fitted directly between the engine and the oil filter.

Figure 8:
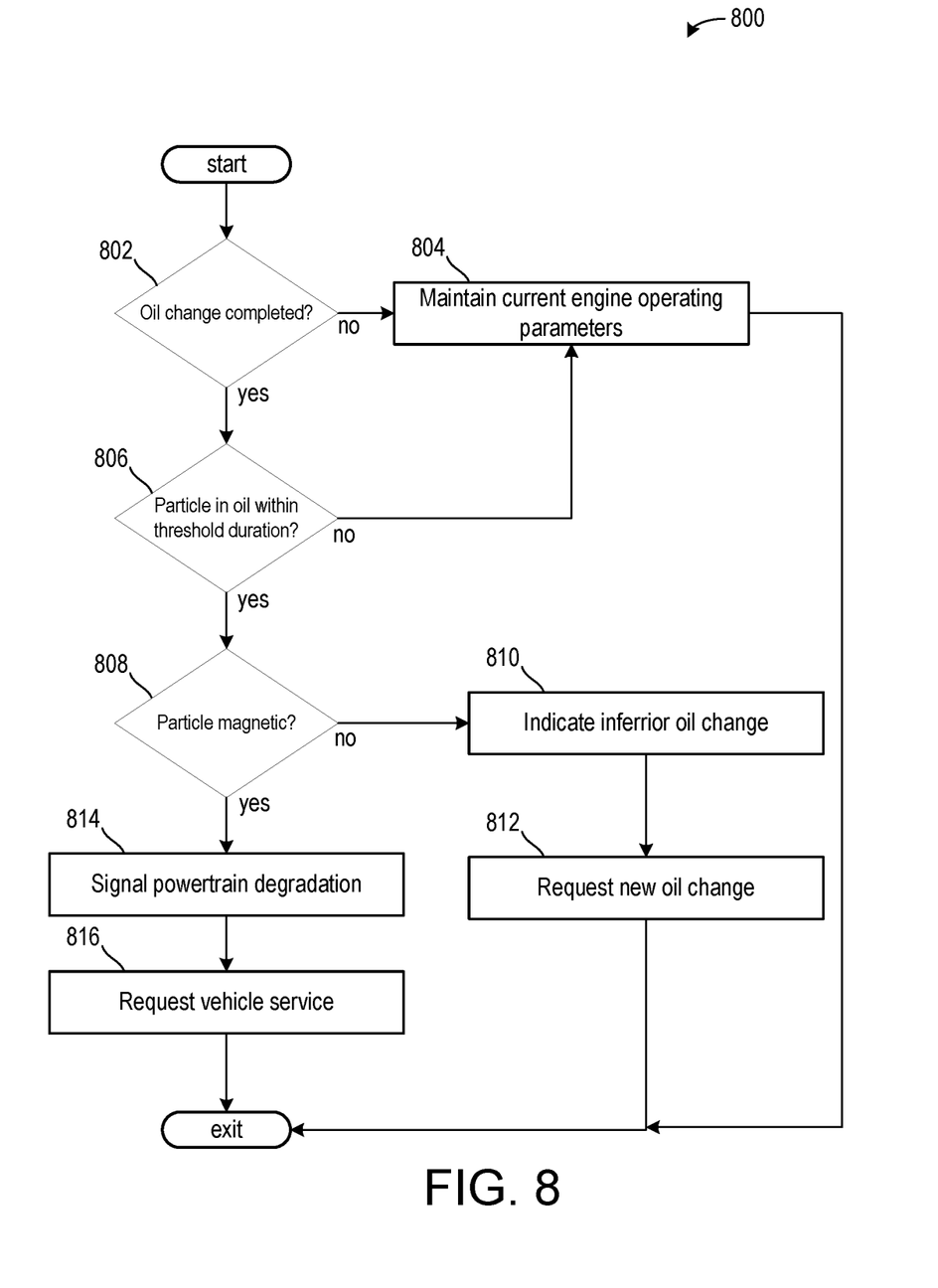
FIG. 8 illustrates a method for determining if a drivetrain component is degraded.

The lubricant detection device may comprise inductive sensors and/or optical sensors with a particle capturing device arranged therebetween. In one example, the particle capturing device comprises inductive features. In another example, the particle capturing device is an oil filter. In some examples, the lubricant detection device may comprise a mix of optical and inductive (e.g., magnetic) devices for diagnostic purposes, as shown in the method of FIG. 8.

Figure 4A:
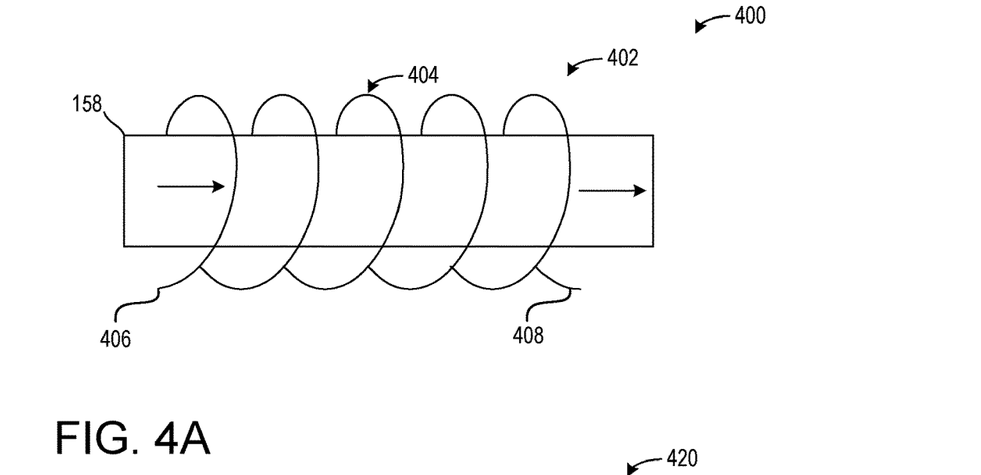
FIG. 4A illustrates a first example of a sensor of a detection device.
Figure 4B:
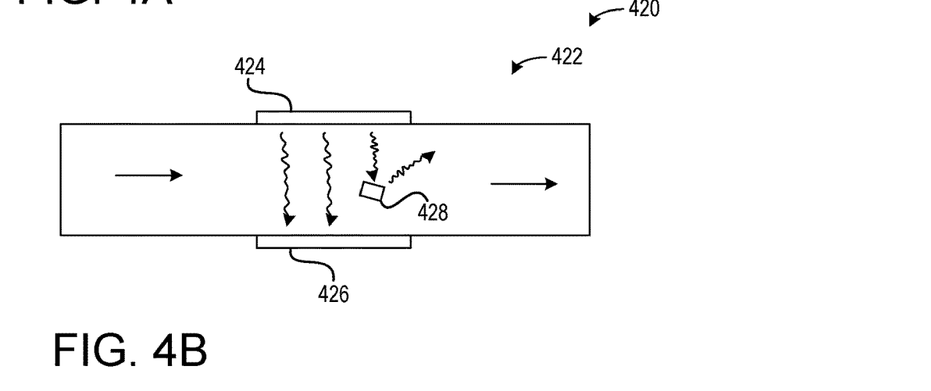
FIG. 4B illustrates a second example of the sensor of the detection device.
Figure 4C:
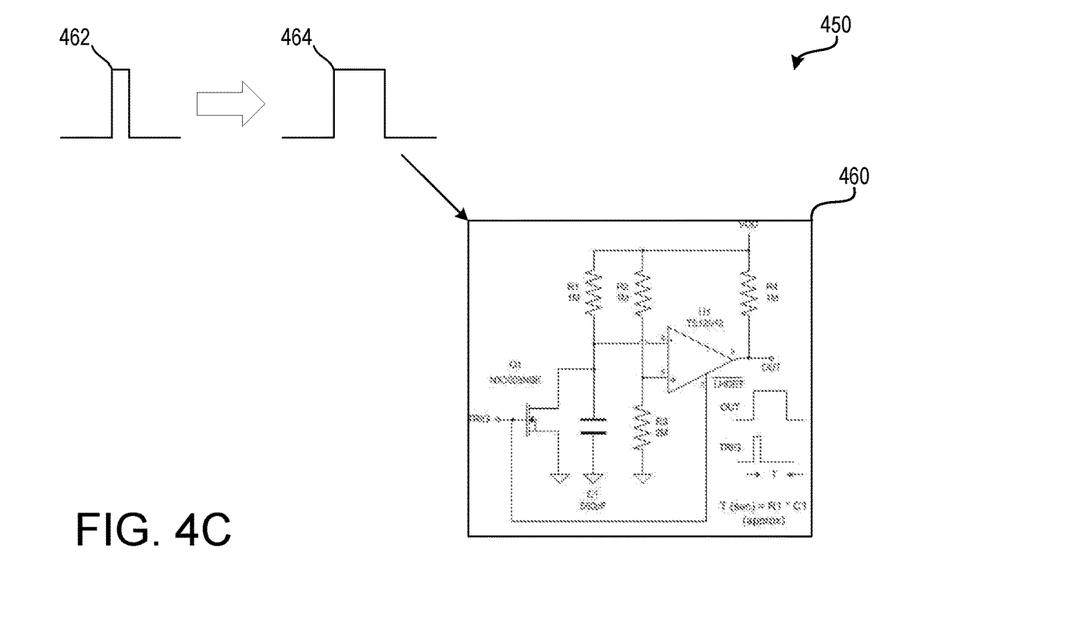
FIG. 4C illustrates a circuit of the sensor of the detection device.

FIG. 4A shows an example of an inductive sensors and FIG. 4B shows an example of an optical, laser, or infrared sensor. FIG. 4C shows a one-shot latch circuit comprising memory to store a signal deviating from a baseline value, wherein the signal may be transformed (e.g., magnified) to a desired value for analysis.

Figure 5:
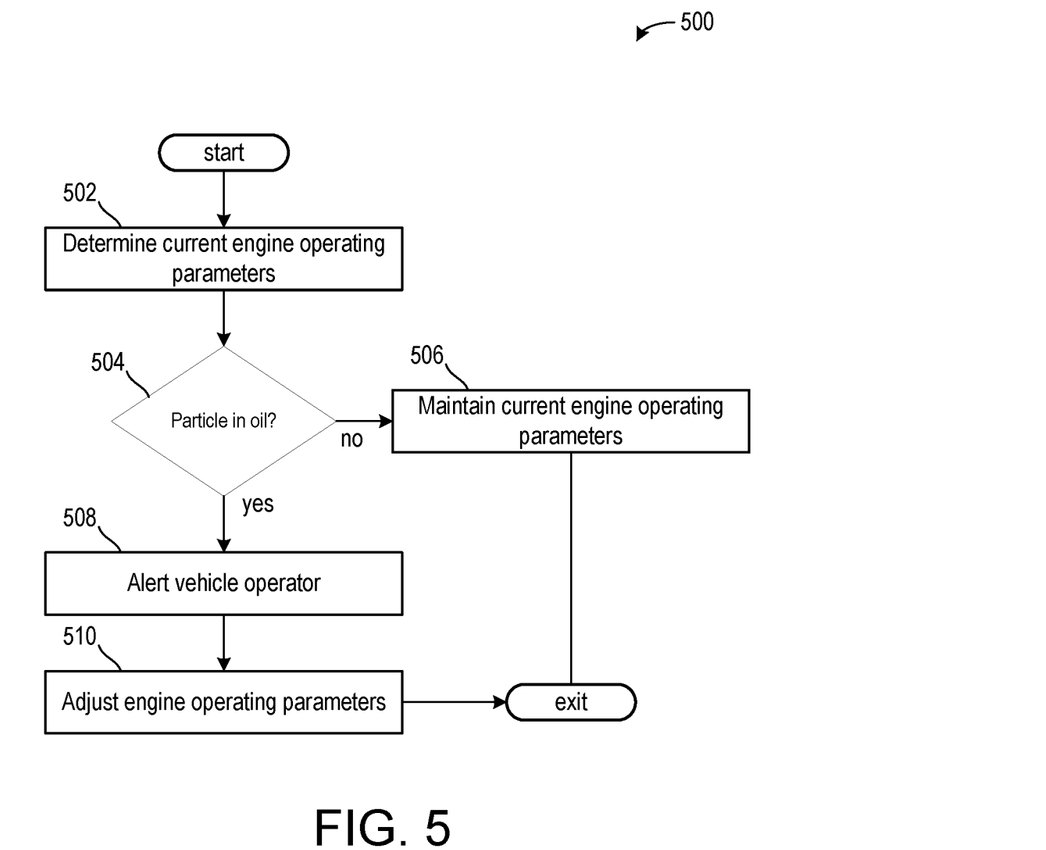
FIG. 5 illustrates a method for determining if a particle is in a lubricant.
Figure 6:
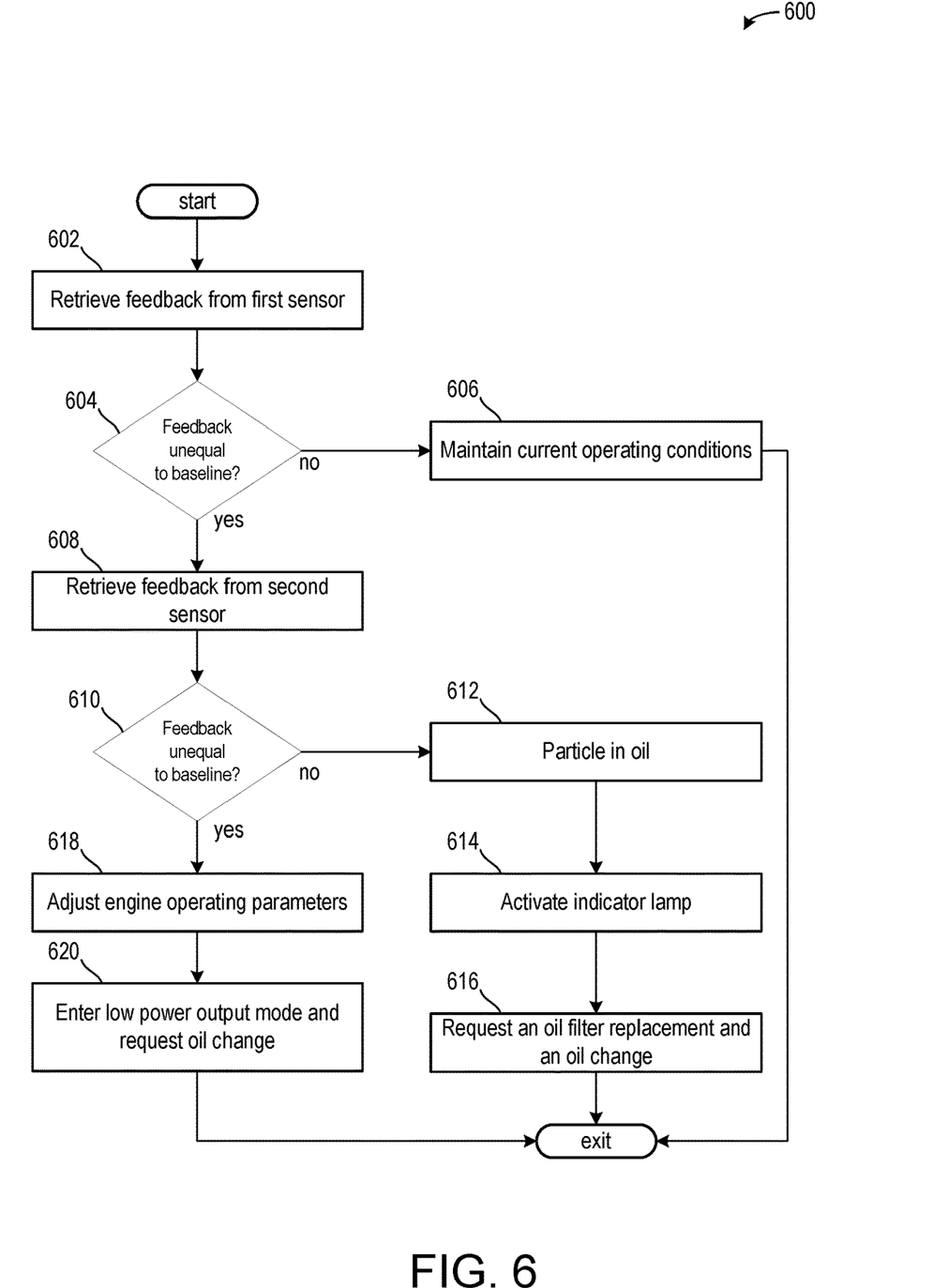
FIG. 6 illustrates a method for adjusting engine operating parameters in response to feedback from the first or second sensors of the detection device.
Figure 7:
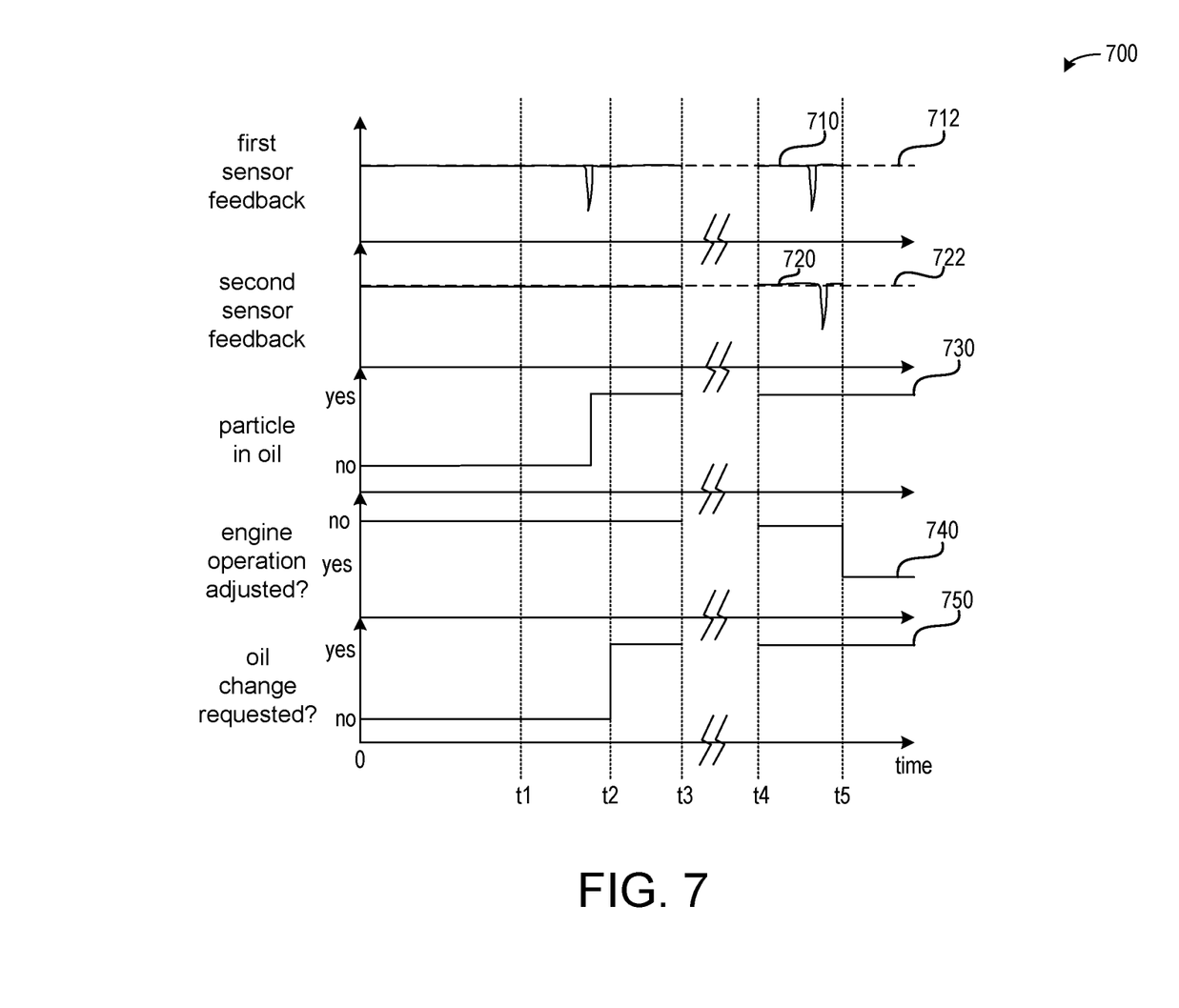
FIG. 7 illustrates an engine operating sequence graphically displaying a prophetic example of engine operating parameters being adjusted in response to feedback from the first and second sensors.

A method for determining if a particle is in the lubricant (e.g., oil) is shown in FIG. 5. FIG. 6 illustrates a method for adjusting engine operating parameters in response to feedback from one or more of the first and second sensors of a lubricant detection device. FIG. 7 illustrates an engine operating sequence graphically displaying various engine operating parameters along with sensor feedback from a sensor of a lubricant detection device.

FIGS. 1-3 show example configurations with relative positioning of the various components. If shown directly contacting each other, or directly coupled, then such elements may be referred to as directly contacting or directly coupled, respectively, at least in one example. Similarly, elements shown contiguous or adjacent to one another may be contiguous or adjacent to each other, respectively, at least in one example. As an example, components laying in face-sharing contact with each other may be referred to as in face-sharing contact. As another example, elements positioned apart from each other with only a space therebetween and no other components may be referred to as such, in at least one example. As yet another example, elements shown above/below one another, at opposite sides to one another, or to the left/right of one another may be referred to as such, relative to one another. Further, as shown in the figures, a topmost element or point of element may be referred to as a "top" of the component and a bottommost element or point of the element may be referred to as a "bottom" of the component, in at least one example. As used herein, top/bottom, upper/lower, above/below, may be relative to a vertical axis of the figures and used to describe positioning of elements of the figures relative to one another. As such, elements shown above other elements are positioned vertically above the other elements, in one example. As yet another example, shapes of the elements depicted within the figures may be referred to as having those shapes (e.g., such as being circular, straight, planar, curved, rounded, chamfered, angled, or the like). Further, elements shown intersecting one another may be referred to as intersecting elements or intersecting one another, in at least one example. Further still, an element shown within another element or shown outside of another element may be referred as such, in one example. It will be appreciated that one or more components referred to as being "substantially similar and/or identical" differ from one another according to manufacturing tolerances (e.g., within 1-5% deviation).

FIG. 1 shows a schematic depiction of a hybrid vehicle system 6 that can derive propulsion power from engine system 8 and/or an on-board energy storage device. An energy conversion device, such as a generator, may be operated to absorb energy from vehicle motion and/or engine operation, and then convert the absorbed energy to an energy form suitable for storage by the energy storage device.

Engine system 8 may include an engine 10 having a plurality of cylinders 30. Engine 10 includes an engine intake 23 and an engine exhaust 25. Engine intake 23 includes an air intake throttle 62 fluidly coupled to the engine intake manifold 44 via an intake passage 42. Air may enter intake passage 42 via air filter 52. Engine exhaust 25 includes an exhaust manifold 48 leading to an exhaust passage 35 that routes exhaust gas to the atmosphere. Engine exhaust 25 may include one or more emission control devices 70 mounted in a close-coupled position or in a far underbody position. The one or more emission control devices may include a three-way catalyst, lean NOx trap, diesel particulate filter, oxidation catalyst, etc. It will be appreciated that other components may be included in the engine such as a variety of valves and sensors, as further elaborated in herein. In some embodiments, wherein engine system 8 is a boosted engine system, the engine system may further include a boosting device, such as a turbocharger (not shown).

The vehicle system 6 further comprises a lubricant system 150 comprising a lubricant sump 152 housing a lubricant pump 154 for pumping lubricant 156 through a lubricant conduit 158. In one example, the lubricant 156 is oil and the lubricant system 150 is an oil system. The lubricant conduit 158 and/or the oil conduit 158 may comprise a lubricant detection device 160 comprising one or more sensors for detecting a particle in the oil 156. In one example, the lubricant detection device 160 detects oil flowing from the engine 10 to the oil sump 152. In another example, the lubricant detection device 160 detects oil flowing from the oil sump 152 to the engine 10.

Vehicle system 6 may further include control system 14. Control system 14 is shown receiving information from a plurality of sensors 16 (various examples of which are described herein) and sending control signals to a plurality of actuators 81 (various examples of which are described herein). As one example, sensors 16 may include exhaust gas sensor 126 located upstream of the emission control device, temperature sensor 128, and pressure sensor 129. Other sensors such as additional pressure, temperature, air/fuel ratio, and composition sensors may be coupled to various locations in the vehicle system 6. As another example, the actuators may include the throttle 62.

Controller 12 may be configured as a conventional microcomputer including a microprocessor unit, input/output ports, read-only memory, random access memory, keep alive memory, a controller area network (CAN) bus, etc. Controller 12 may be configured as a powertrain control module (PCM). The controller may be shifted between sleep and wake-up modes for additional energy efficiency. The controller may receive input data from the various sensors, process the input data, and trigger the actuators in response to the processed input data based on instruction or code programmed therein corresponding to one or more routines.

In some examples, hybrid vehicle 6 comprises multiple sources of torque available to one or more vehicle wheels 59. In other examples, vehicle 6 is a conventional vehicle with only an engine, or an electric vehicle with only electric machine(s). In the example shown, vehicle 6 includes engine 10 and an electric machine 51. Electric machine 51 may be a motor or a motor/generator. A crankshaft of engine 10 and electric machine 51 may be connected via a transmission 54 to vehicle wheels 59 when one or more clutches 56 are engaged. In the depicted example, a first clutch 56 is provided between a crankshaft and the electric machine 51, and a second clutch 56 is provided between electric machine 51 and transmission 54. Controller 12 may send a signal to an actuator of each clutch 56 to engage or disengage the clutch, so as to connect or disconnect crankshaft from electric machine 51 and the components connected thereto, and/or connect or disconnect electric machine 51 from transmission 54 and the components connected thereto. Transmission 54 may be a gearbox, a planetary gear system, or another type of transmission. The powertrain may be configured in various manners including as a parallel, a series, or a series-parallel hybrid vehicle.

Electric machine 51 receives electrical power from a traction battery 61 to provide torque to vehicle wheels 59. Electric machine 51 may also be operated as a generator to provide electrical power to charge battery 61, for example during a braking operation.

Turning now to FIG. 2, it shows a first example 200 of the lubricant detection system 160. As such, components previously introduced may be similarly numbered in this figure and subsequent figures. The lubricant detection system 160 is arranged along the lubricant conduit 158 as described above.

The lubricant conduit 158 may be shaped to flow lubricant, such as oil, through the lubricant detection system 160. Herein, the lubricant conduit 158 and the lubricant detection system 160 may be interchangeably referred to as the oil conduit 158 and the oil detection system 160, respectively. The oil conduit 158 may flow oil in a first direction parallel to arrow 231 into the oil detection system 160. As the oil flows toward a first sensor 212, the oil turns and flows in a second direction, shown by arrow 232, perpendicular to the first direction. The oil again turns and flows in the first direction before turning in a third direction, shown by arrow 233, perpendicular to the first direction and opposite the second direction. The oil flows through the first sensor 212 as it flows in the third direction.

The first sensor 212 may be a most upstream sensor and/or component of the oil detection system 160. Herein, upstream and downstream may be used to describe an arrangement of components relative to a direction of lubricant flow. For example, the first sensor 212 is more upstream of a second sensor 214 and a particle capturing device 216. Thus, lubricant may contact or flow through the first sensor 212 before contacting or flowing through the second sensor 214 and the particle capturing device 216.

The oil may leave the first sensor 212 flowing in the third direction before turning and flowing in the second direction toward the particle capturing device 216. As such, the particle capturing device 216 is downstream of the first sensor 212 and upstream of the second sensor 214. Said another way, the particle capturing device 216 is arranged between the first sensor 212 and the second sensor 214.

The oil may flow past the particle capturing device 216 where it turns from the first direction to the second direction, wherein the oil flows to the second sensor 214 in the second direction. The oil may flow through the second sensor 214 in the second direction. After the oil leaves the second sensor 214, the oil turns and flows in the first direction. The oil then turns in the third direction and turns again to flow in the first direction as it leaves the lubricant detection system 160.

By undulating the oil conduit 158 in the lubricant detection system 160, a packaging size of the lubricant detection system 160 may be reduced relative to an oil conduit with a linear flow. As such, a packaging constraint imposed by the lubricant detection system 160 may be relatively low. It will be appreciated that the oil conduit 158 may comprise a variety of shapes without departing from the scope of the present disclosure. For example, the oil conduit 158 may comprise a linear, curved, spiraled, or the like shaped flow path.

In the lubricant detection system 160, the first sensor 212 and the second sensor 214 may detect if a particle is in the oil flow. In one example, if the first sensor 212 and the second sensor 214 are both inductive or coil based sensors, then the first and second sensors 212, 214 may only detect if ferromagnetic particles are in the oil. In some examples, additionally or alternatively, if one or both of the first and second sensors 212, 214 are laser, optic, or infrared spectroscopy (IR) sensors, then all particles different than oil may be monitored as feedback received by a receiver may be shifted due to a compound other than oil being present. The first sensor 212 and the second sensor 214 are described in greater detail with respect to FIGS. 4A and 4B. In one example, the lubricant detection system 160 may be disposable and replaceable.

The particle capturing device 216 may be one or more of a magnet or a filter. In one example, the particle capturing device 216 is a magnet capturing ferromagnetic particles in the oil. As another example, the particle capturing device 216 is an oil filter, which may be similar to an oil filter arranged between the oil conduit 158 and the engine 10. In one example, to further decrease packaging restraints of the lubricant detection system 160, the particle capturing device 216 is the oil filter already arranged onboard the vehicle (e.g., vehicle system 6).

In one example and as will be discussed in the methods below, feedback from the first sensor 212 may indicate a particle is in the oil. The particle may or may not be captured by the particle capturing device 216 depending on properties of the particle and/or a state of the particle capturing device 216. If the particle is captured by the particle capturing device 216, then the second sensor 214 may not detect a particle in the oil. As such, engine operating parameters may be adjusted based on a particle being in the oil, but not being able to flow to the engine and other lubricated components. In one example, engine operating parameters are adjusted to decrease an engine power output. For example, a fuel injection amount may decrease. Additionally, a message to a vehicle operator may be sent, requesting an oil change. If the particle capturing device 216 is fully loaded or degraded, then the particle may reach the second sensor 214, wherein engine operating parameters are adjusted based on the particle being able to reach the engine and other lubricated components. In one example, adjusting the engine operating parameters includes adjusting the engine operation to a low power output mode. Adjusting engine operating parameters in response to feedback from the first and second sensors is described in greater detail below.

Turning now to FIG. 3, it shows a second example 300 of the lubricant detection system 160. The second example 300 may differ from the first example 200 of FIG. 2 in that the second example 300 is shaped to physically couple to each of the engine 10 and an oil filter 310. More specifically, the engine 10 comprises an engine bolt 302 and the oil filter 310 comprises a bolt receiving opening 304 shaped to receive the engine bolt 302. The second example 300 of the lubricant detection system 160 comprises where the lubricant detection system 160 has a bolt receiving opening 306 shaped to receive the engine bolt 302 and a detection system bolt 308 shaped to couple with the bolt receiving opening 304. As such, the lubricant detection system 160 may be arranged between the engine 10 and the oil filter 310. In this way, the lubricant detection system 160 may be retrofitted to previously manufactured vehicles and in direct face-sharing contact with the engine 10 and the oil filter 310 with no intervening components.

The second example 300 of the lubricant detection system 160 further comprises where only a single oil sensor 322 is arranged in the lubricant detection system 160. In one example, feedback from the single oil sensor 322 may be interpreted similarly to feedback from the second sensor 214 of FIG. 2. That is to say, if the single oil sensor 322 detects a particle in the oil, then the engine operating parameters may be adjusted to decrease an engine power output.

The lubricant detection system 160 comprises passages for allowing oil to flow from the engine to the oil filter and vice-versa. More specifically, the lubricant detection system 160 comprises a first passage 332 for flowing oil from the engine 10 to the oil filter 310. The lubricant detection system 160 further comprises a second passage 334 for flowing oil from the oil filter 310 to the engine 10. The second passage 334 may house the single oil sensor 322 and a particle capturing device 324. In the example of FIG. 3, the particle capturing device 324 is a magnet. However, the particle capturing device 324 may also be an oil filter without departing from the scope of the present disclosure. As such, the particle capturing device 324 may be a smaller version of the oil filter 310.

In the example of FIG. 3, if a particle is sensed by the single oil sensor 322, then a controller may determine that the oil filter 310 is degraded and no longer configured to capture particles. Furthermore, detection of the particle via the single oil sensor 322 may result in engine operating parameters being adjusted to a low power mode.

In some examples, additionally or alternatively, the single oil sensor 322 may be a first sensor, wherein the lubricant detection system 160 further comprises a second optional sensor 326 downstream of the particle capturing device 324. As such, the single oil sensor may be used similarly to the first sensor 212 of FIG. 2 and the second sensor may be used similarly to the second sensor 214 of FIG. 2.

It will be appreciated that the first example 200 of FIG. 2 may comprise the bolt and receiving hole couplings of the second example 300, such that the first example of the lubricant detection system 160 may be fitted between the engine 10 and the oil filter 310.

Turning now to FIG. 4A, it shows a first embodiment 400 of an oil sensor 402, which may be used similarly to the first oil sensor 212 of FIG. 2, the second oil sensor 214 of FIG. 2, and/or the single oil sensor 322 of FIG. 3. The oil sensor 402 comprises a coil 404 extending around a diameter of the oil conduit 158. The coil 404 may comprise a positive end 406 and a negative end 408, allowing the coil to produce an electromagnetic field. If oil free of particles flows through the oil sensor 402, then a voltage feedback provided by the oil sensor 402 may be equal to approximately zero. However, if particles are present in the oil, then a voltage feedback provided by the oil sensor 402 may be a positive voltage value. In one example, the oil sensor 402 detects a positive voltage feedback if the particle is a ferromagnetic particle. As such, non-magnetic particles may not be detected by the oil sensor 402.

In some examples, the oil sensor 402 may be configured to measure an absolute value of a current induced in the coil 404. By doing this, a particle released from a particle capturing device (e.g., particle capturing device 216 of FIG. 2 or 324 of FIG. 3) may still be sensed. The particle may be released via contact from oil flow or other particles in the oil, wherein the particle may be dislodged from the particle capturing device. At any rate, if the particle capturing device is a magnetic particle capturing device, then the dislodged particle may comprise an amount of transient magnetic retention, wherein the dislodged particle may create a magnetic field. If a sensor is a magnetic sensor and unable to measure an absolute value of a current induced, then based on an angle of the particle passing through the coil 404, the current induced may be positive and the particle detected, or negative and the particle not detected. As such, if the sensor downstream of a magnetic particle capturing device is a magnetic sensor, then it may be desired to configure the magnetic sensor to sense an absolute value of a current generated by a particle passing therethrough.

Turning now to FIG. 4B, it shows a second embodiment 420 of an oil sensor 422, which may be used similarly to the first oil sensor 212 of FIG. 2, the second oil sensor 214 of FIG. 2, and/or the single oil sensor 332 of FIG. 3. The oil sensor 422 comprises an emitter 424 and a receiver 426. As such, the oil sensor 422 may be an infrared, optic, or laser detection device. In this way, the emitter 424 may be an infrared, optic, or a laser emitter and the receiver 426 may be a corresponding infrared, optic, or laser emitter. The emitter 424 may direct one or more photons at the receiver 426. When oil free of particles flows through the oil sensor 422, the receiver 426 may sense a first voltage and/or a first signal. If a particle, such as particle 428, is arranged in the oil, then the receiver 426 may receive a second signal different than the first signal, resulting in feedback indicating the particle 428 is in the oil. It will be appreciated that the oil sensor 422 may be configured to detect both ferromagnetic and non-magnetic particles.

In some examples, a lubricant detection system, such as lubricant detection system 160 of FIGS. 1, 2, and 3, may comprise a first oil sensor that is an infrared, optic, or a laser detection sensor and a second oil sensor that is an induction sensor. In one example, the first oil sensor is arranged upstream of the second sensor, where a particle capturing device is arranged between the first and second oil sensors. As such, the first oil sensor may provide feedback if a particle is in the oil regardless of whether the particle is magnetic or non-magnetic. The second oil sensor may provide feedback indicating if the particle is magnetic or non-magnetic Additionally or alternatively, each of the first and second sensors may be infrared, optic, or laser detection sensors. However, the particle capturing device may be a magnet. As such, if a particle is sensed by the second oil sensor, then it may be determined that the particle is non-magnetic. Determining a magnetism of the particle is described in greater detail with respect to FIG. 8.

Turning now to FIG. 4C, it shows an embodiment 450 of a latch circuit 460, wherein the latch circuit may receive a first signal 462 from an oil sensor, such as first or second sensors 212, 214 of FIG. 2, single sensor 322 of FIG. 3, oil sensor 402 of FIG. 4A, and/or oil sensor 422 of FIG. 4B. The latch circuit 460 may manipulate the first signal 462 into a desired second signal 464, wherein the latch circuit 460 may store the second signal 464 in memory until it is received by a controller (e.g., controller 12 of FIG. 1) to be analyzed.

The circuit 460 may receive an input, which may correspond to feedback from a first or second sensor, wherein the input may be manipulated into an output. The output may be compared to a threshold (e.g., a baseline and/or a stable state), wherein if a difference is determined then a particle may be in the oil. The circuit 460 may be included in the controller 12 of FIG. 1.

The first signal 462 may be identified due to its deviation from a baseline value (e.g., a stable state) of the latch circuit 460 as a sensor samples the oil flow repeatedly, thereby indicating a change in system settings. In the example of FIG. 4C, the change is in response to a particle being in the oil and flowing through the lubricant detection system.

The sensors may be calibrated to sample the oil in pulses based on an oil velocity, the oil velocity based on engine operating parameters. For example, if the engine is a four-cylinder engine operating at 1500 rotations per minute (rpm) with a 50% open throttle, then oil velocity may be equal to about 0.41 cm$^3$/min. During such an operating condition, the sensors may sample the oil with a minimum sample rate of 1000 Hz (e.g., 0.001 ms). In one example, the sample rate of the sensors may increase as the throttle position and/or engine rpm increase. Additionally or alternatively, the sample rate may be kept constant independent of engine operating parameters.

Turning now to FIG. 5, it shows a method 500 for determining if a particle is in a lubricant, such as oil. Instructions for carrying out method 500 and the rest of the methods included herein may be executed by a controller based on instructions stored on a memory of the controller and in conjunction with signals received from sensors of the engine system, such as the sensors described above with reference to FIG. 1. The controller may employ engine actuators of the engine system to adjust engine operation, according to the methods described below.

The method 500 begins at 502, which includes determining, estimating, and/or measuring current engine operating parameters. The current engine operating parameters may include one or more of but are not limited to a throttle position, an engine temperature, an engine speed, a manifold vacuum, a boost, and an air/fuel ratio.

The method 500 proceeds to 504, which includes determining if a particle is in the oil. A particle may be in the oil if feedback from an oil sensor arranged in the lubricant detection system deviates from a baseline value. As described above, if the oil sensor is a magnetic sensor, a voltage feedback from the oil sensor may be positive and therefore higher than its baseline value (e.g., zero volts) when a ferromagnetic particle passes through the oil sensor. As another example, if the oil sensor is an infrared, an optic, or a laser sensor, then a signal sensed as a particle passes through the oil sensor may deviate from its baseline value. In one example, this may result in a decreased voltage value sensed by the oil sensor.

If a particle is not in the oil and feedback from the oil sensor is equal to a baseline value when oil free of particles flows through the oil sensor, then the method 500 proceeds to 506 to maintain current engine operating parameters and does not alert the vehicle operator of a particle being in the oil.

However, if a particle is sensed in the oil, then the method 500 proceeds to 508 to alert the vehicle operator. This may include activating an indicator lamp. Additionally or alternatively, the vehicle operator may receive a text, email, phone call, or other form of electronic communication indicating a particle is in the oil. This may be executed via a wireless communication, cellular communication, or other short and/or long range form of communication. The electronic communication may further request the vehicle operator to change the oil and/or an oil filter. In some examples, the vehicle operator may select to have an oil change automatically scheduled based on the requested oil change. Automatically scheduling the oil change may comprise scheduling the oil change based on a vehicle operator schedule and vehicle service shops arranged along a travel path of the vehicle operator. For example, if the vehicle operator is scheduled to go to a physician's office on a Saturday, the oil change may be scheduled following the appointment at the physician's office. Additionally, a service shop selected may be a service shop nearest a travel path from the physician's office to the vehicle operator's home.

The method 500 proceeds to 510, which includes adjusting engine operating parameters in response to the particle being in the oil. Adjusting the engine operating parameters may include adjusting one or more of a fuel injection and a spark (e.g., if the engine is a spark ignited engine). Additionally or alternatively, the vehicle may be a hybrid vehicle, wherein an operating mode may be shifted to an all-electric mode. The all-electric mode may comprise fewer moving parts (e.g., only the drivetrain versus the powertrain), thereby decreasing a likelihood and/or a magnitude of degradation. These adjustments are described in greater detail below with respect to FIG. 6.

Turning now to FIG. 6, it shows a method 600 for determining if a particle is in the oil and adjusting engine operating parameters in response to the first and/or second sensors sensing the particle. The method 600 begins at 602, which includes retrieving feedback from a first sensor. The first sensor may be substantially similar to first sensor 212 of FIG. 2, in one example. Feedback from the first sensor may include a first signal that matches a baseline value of the first sensor or a second signal that deviates from the baseline value due to an impurity, such as a particle, being in the oil. Thus, the baseline value corresponds to oil free of impurities flowing through the first sensor.

The method 600 proceeds to 604, which includes determining if the feedback from the first sensor deviates from the baseline value. If the feedback is equal to the baseline value, then the method 600 proceeds to 606 to maintain current engine operating parameters and does not alert that vehicle operator that a particle is in the oil. If the feedback is unequal to the baseline value, then the method 600 proceeds to 608, which includes retrieving feedback from the second sensor. The feedback may be greater than or less than the baseline value. For example, if the first sensor is a magnetic sensor, the feedback may be greater than the baseline value if the particle is a metal particle. Alternatively, if the first sensor is an infrared, an optic, or a laser detection sensor, then the feedback may be less than the baseline value if a particle is in the oil, wherein the particle may be magnetic or non-magnetic.

The method 600 proceeds to 610, which includes determining if the feedback from the second sensor is unequal to a baseline value. In one example, if the first sensor and the second sensor are identical, then the baseline values of the two sensors may be substantially identical. However, if the first sensor and the second sensor are different (e.g., one if an induction sensor and the other is a laser sensor), then the baseline values of each sensor may be different. If the feedback from the second sensor is equal to the baseline value, then the method 600 proceeds to 612, which includes determining a particle is in the oil. At 614, the method includes activating an indicator lamp in a dash panel of the vehicle. Additionally or alternatively, activating the indicator lamp may further include alerting the vehicle operator may include a letter, text, email, phone call, or other form of communication.

The method 600 proceeds to 616, which may include requesting an oil filter replacement and an oil change. As described above, the requesting may further include example service shops at which the vehicle operator may receive the requested vehicle service. The example service shops may be selected based on a proximity to one or more of frequently visited locations, frequently used travel paths, and availability of the service shop based on a vehicle operator schedule.

If the feedback is unequal to the baseline, then the particle is sensed by each of the first sensor and the second sensor. In such an example, the method 600 proceeds to 618, adjusting engine operating parameters. The engine operating parameters may be adjusted based on a particle being in the oil and being able to reach various components of the powertrain downstream of the lubricant detection system. As described above, the particle capturing device may be a magnet or an oil filter. As such, the engine operating parameters may be adjusted to decrease an engine power output. The adjustments may include decreasing boost, decreasing a fuel injection amount, and adjusting a spark timing (e.g., retarding). Additionally or alternatively, a compression ratio of a combustion chamber may be reduced. The adjustments may be maintained until the oil change request is fulfilled.

The particle capturing device may not capture the particle due to the particle being non-magnetic and the particle capturing device being a magnet, in one example. In another example, the particle capturing device may be fully loaded from capturing particles and may not comprise storage space to retain the particle. As a further example, the particle capturing device may be degraded, wherein a leak may develop in the particle capturing device, thereby allowing particles to flow therethrough. As a further example, a particle captured by the particle capturing device may be dislodged due to turbulent oil flow and/or due to another particle colliding into the particle capturing device and releasing already captured particles.

The method 600 proceeds to 620, which includes entering a low power output mode and demanding an oil change prior to a subsequent engine start. The low power output mode may be maintained until the oil change is completed.

In some examples of the method 600, the indicator lamp and/or the engine operating parameter adjustments may be activated in response to a number of particles flowing through the first sensor. A counter may track a number of particles that have passed through the first sensor. In one example, the indicator lamp may be activated after a first threshold number of particles have passed through the first sensor. The engine operating parameters may be adjusted in response to a second threshold number of particles passing through the first sensor. In this way, the engine operating parameters may be adjusted without the second sensor sensing a particle. Additionally or alternatively, if the second sensor senses a particle before either the first threshold number of the second threshold number is reached, then the engine operating parameters may be adjusted and the indicator lamp activated. The first threshold number and the second threshold number may both be positive, non-zero numbers, wherein the first threshold number is less than the second threshold number.

Turning now to FIG. 7, it shows a prophetic engine operating sequence illustrating a graph 700 plotting various vehicle operating conditions. Plot 710 illustrates a first sensor feedback and dashed line 712 illustrates a first sensor baseline value. The first sensor feedback may track, and therefore occlude, the first sensor baseline value when a particle is not detected in the oil. Plot 720 illustrates a second sensor feedback and dashed line 722 illustrates a second sensor baseline value. The second sensor feedback may track, and therefore occlude, the second sensor baseline value when a particle is not detected in the oil. In the example of FIG. 7, each of the first sensor and the second sensor are infrared, optic, or laser sensors. As such, deviation from a baseline value may include where feedback is less than the baseline value. Plot 730 illustrates if a particle is sensed in the oil. Plot 740 illustrates if engine operating parameters are adjusted. Plot 750 illustrates if an oil change is requested. Time increases from a left to a right side of the figure.

Prior to t1, the first sensor feedback (plot 710) is equal to the first sensor baseline value (dashed line 712). Additionally, the second sensor feedback (plot 720) is equal to the second sensor baseline value (dashed line 722). As such, a particle is not detected in the oil (plot 730), and engine operating parameters are not adjusted (plot 740) and an oil change is not requested (plot 750).

Between t1 and t2, the first sensor feedback deviates from the first sensor baseline value, and as such, it is determined that a particle is in the oil. The second sensor feedback is substantially equal to the second sensor baseline value, thereby indicating a particle is not in the oil. However, the second sensor may not sense the particle due to a particle capturing device being arranged between the first and second sensors capturing the particle. As such, engine operation is not adjusted in response to a particle being in the oil but unable to reach various components of the powertrain. At t2, an oil change is requested, wherein requesting the oil change may further comprise requesting an oil filter change. The particle may be in the oil due to the oil filter degrading (e.g., being fully loaded and/or developing a leak in the form of a hole, crack, or the like). Between t3 and t4, an amount of time passes.

At t4, the oil change is still requested, thereby indicating that an oil change has not yet occurred. Between t4 and t5, the first sensor feedback deviates from the first sensor baseline value, thereby indicating a particle is in the oil. In one example, the particle sensed between t4 and t5 is different than the particle sensed between t1 and t2. Furthermore, the particle is not captured by the particle capturing device and reaches the second sensor, wherein the second sensor feedback deviates from the second sensor baseline feedback. As such, the particle may reach components of the powertrain.

At t5, the engine operating parameters are adjusted so that the engine enters a low power output mode, as described above. The oil change request remains active. In one example, the engine operating parameter may be adjusted to switch a vehicle operating mode to an all-electric mode. After t5, the engine operating parameter adjustments may be maintained until an oil change is completed.

Turning now to FIG. 8, it shows a method 800 for determining if an oil change was inferior or if a powertrain component is actively shedding particles into the oil. The method 800 begins at 802, which includes determining if an oil change is completed. The oil change may be completed if an oil pan plug was removed, the oil drained, and the oil pan refilled with oil. A service technician may indicate the oil change is completed or an oil volume sensor may indicate a change in oil volume corresponding to the oil change (e.g., oil volume decreases by an amount and is replenished by the amount). If the oil change is not completed, then the method 800 proceeds to 804, which includes maintaining current engine operating parameters. As described above, if the oil change is request in response to a particle being detected, engine operating parameters may be adjusted to decrease an engine power output by adjusting a fuel injection amount and/or spark timing.

If the oil change is completed, then the method 800 proceeds to 806, which includes determining if a particle is in the oil within a threshold duration, similar to 504 of method 500 of FIG. 5. However, 806 differs from 804 in that a threshold duration is tracked following the oil change. In one example, the threshold duration may be based on a lifespan of an oil filter and/or an average amount of time before a particle enters the oil. If a particle is not in the oil and a time elapsed following the oil change is less than or equal to the threshold duration, then the oil change was executed as desired and the powertrain may not be actively shedding particles. The method 800 proceeds to 804 as described above.

If a particle is in the oil and the time elapsed is less than the threshold duration, then the method 800 proceeds to 808, which may include determining if the particle is magnetic. In this way, a particle entered the oil more quickly than expected and may be due to an inferior oil change (e.g., not all of the oil was properly drained) or a powertrain component releasing particles. The particle may be determined to be magnetic in response to feedback from an oil sensor configured to be an induction oil sensor. As such, voltage feedback from the induction sensor may comprise a positive value. Additionally or alternatively, the particle may be magnetic if a first sensor, upstream of a second sensor with a magnet configured as a particle capturing device arranged therebetween, senses the particle and the second sensor does not. As such, the magnetic particle is captured by the magnet thereby indicating a ferromagnetic particle is released into the oil. The particle may not be magnetic if the particle is not sensed by the induction sensor or if the particle is not captured by the magnetic particle capturing device. In examples of the method 800 for a lubricant detection system free of an inductive device, step 808 may be omitted as it may not be determined if the particle is magnetic with only optical sensors and an oil filter arranged therebetween.

If the particle is not magnetic, then the method 800 proceeds to 810, which includes indicating the oil change was inferior and/or incomplete. A flag may be set such that when the vehicle operator returns to the service shop, the service technician may see the flag. In this way, the vehicle operator may not be charged for an additional oil change. The method 800 proceeds to 812, which includes requesting a new oil change.

If the particle is magnetic, then the method 800 proceeds to 814, which includes signaling a powertrain degradation. This may further include adjusting engine operating parameters similar to the adjustments described above to decrease an engine power output to mitigate particle release and further degradation to other powertrain components.

The method 800 proceeds to 816, which includes requesting a vehicle service. The vehicle service may include inspection of the various powertrain components to determine which, if any, of the components is shedding particles.

In this way, a lubricant detection device comprises one or more sensors for detecting a particle in a lubricant, such as oil. The lubricant detection device may comprise one or more sensors and a particle capturing device. The technical effect of arranging a lubricant detection device in a lubricant conduit is to detect if a particle is in the lubricant and adjust engine operating parameters in response to the particle.

An embodiment of a system comprises a lubricant passage comprising a particle capturing device arranged between a first sensor and a second sensor and a controller with instructions stored on non-transitory memory thereof that when executed enable the controller to adjust engine operating parameters in response to feedback from the first and second sensors. A first example of the system further includes where engine operating parameters are adjusted in response to feedback from the first sensor include activating an indicator lamp.

A second example of the system, optionally including the first example, further includes where engine operating parameters are adjusted in response to feedback from the second sensor include adjusting one or more of a fuel injection and a spark timing.

A third example of the system, optionally including any of the above examples, further includes where the first sensor and the second sensor are one or more of an induction sensor, an infrared sensor, a laser sensor, and an optical sensor.

A fourth example of the system, optionally including any of the above examples, further includes where the particle capturing device is an oil filter.

A fifth example of the system, optionally including any of the above examples, further includes where the particle capturing device is a magnet.

A sixth example of the system, optionally including any of the above example, further includes where the first sensor is one or more of an infrared sensor, a laser sensor, and an optical sensor, wherein the second sensor is an induction sensor.

An embodiment of a vehicle system comprises a lubricant detection device comprising a particle capturing device arranged between a first sensor and a second sensor, the particle capturing device comprising a magnet and a controller with instructions stored on non-transitory memory thereof that when executed enable the controller to activate an indicator lamp in response to a particle being sensed by only the first sensor, and adjust an engine power output in response to the particle being sensed by each of the first and second sensors.

A first example of the vehicle system further includes where the engine power output is adjusted via one or more of decreasing a fuel injection amount, decreasing boost, and retarding spark.

A second example of the vehicle system, optionally including the first example, further includes where an oil change request is signaled in response to the particle being sensed.

A third example of the vehicle system, optionally including any of the above examples, further includes where the oil change request is removed in response to an oil change being completed, the instructions further enable the controller to determine degradation of a powertrain component in response to a magnetic particle being sensed within a threshold time following the oil change.

A fourth example of the vehicle system, optionally including any of the above examples, further includes where the instructions further enable the controller to determine the oil change was inferior in response to a non-magnetic particle being sensed within the threshold time following the oil change.

A fifth example of the vehicle system, optionally including any of the above examples, further includes where the lubricant detection device is arranged between an engine and a filter, wherein the lubricant detection device is in face-sharing contact with the engine and the filter.

A sixth example of the vehicle system, optionally including any of the above examples, further includes where there are no intervening components arranged between the engine, the lubricant detection device, and the filter, and where the lubricant detection device comprises couplings shaped to mate with an engine bolt of the engine and a receiving hole of the filter.

A seventh example of the vehicle system, optionally including any of the above examples, further includes where the first sensor and the second sensor are identical, wherein the first sensor and second sensor are one or more of an infrared sensor, an optical sensor, and a laser sensor.

An embodiment of a method comprises sensing a particle is in an oil flow in response to feedback from a first sensor of an oil detection system, activating an indicator lamp engine operating parameters in response to the first sensor sensing the particle and a second sensor not sensing the particle, the second sensor arranged downstream of the first sensor relative to a direction of the oil flow, wherein an oil filter is arranged between the first sensor and the second sensor, and adjusting engine operating parameters to decrease a fuel injection amount in response to the first sensor and the second sensor sensing the particle.

A first example of the method further includes where signaling an oil change request in response to the first sensor sensing the particle and the second sensor not sensing the particle; further comprising signaling the oil change request and an oil filter replacement request in response to the first sensor and the second sensor sensing the particle.

A second example of the method, optionally including the first example, further includes where the oil flow is flowing from an oil sump to the engine.

A third example of the method, optionally including any of the above examples, further includes where the first sensor and the second sensor are different, wherein the first sensor is a non-inductive sensor selected from one or more of an infrared sensor, an optical sensor, and a laser sensor and the second sensor is an inductive sensor.

A fourth example of the method, optionally including any of the above examples, further includes where the oil filter is the only oil filter of a vehicle.

Note that the example control and estimation routines included herein can be used with various engine and/or vehicle system configurations. The control methods and routines disclosed herein may be stored as executable instructions in non-transitory memory and may be carried out by the control system including the controller in combination with the various sensors, actuators, and other engine hardware. The specific routines described herein may represent one or more of any number of processing strategies such as event-driven, interrupt-driven, multi-tasking, multi-threading, and the like. As such, various actions, operations, and/or functions illustrated may be performed in the sequence illustrated, in parallel, or in some cases omitted. Likewise, the order of processing is not necessarily required to achieve the features and advantages of the example embodiments described herein, but is provided for ease of illustration and description. One or more of the illustrated actions, operations and/or functions may be repeatedly performed depending on the particular strategy being used. Further, the described actions, operations and/or functions may graphically represent code to be programmed into non-transitory memory of the computer readable storage medium in the engine control system, where the described actions are carried out by executing the instructions in a system including the various engine hardware components in combination with the electronic controller.

It will be appreciated that the configurations and routines disclosed herein are exemplary in nature, and that these specific embodiments are not to be considered in a limiting sense, because numerous variations are possible. For example, the above technology can be applied to V-6, I-4, I-6, V-12, opposed 4, and other engine types. The subject matter of the present disclosure includes all novel and non-obvious combinations and sub-combinations of the various systems and configurations, and other features, functions, and/or properties disclosed herein.

As used herein, the term "approximately" is construed to mean plus or minus five percent of the range unless otherwise specified.

The following claims particularly point out certain combinations and sub-combinations regarded as novel and non-obvious. These claims may refer to "an" element or "a first" element or the equivalent thereof. Such claims should be understood to include incorporation of one or more such elements, neither requiring nor excluding two or more such elements. Other combinations and sub-combinations of the disclosed features, functions, elements, and/or properties may be claimed through amendment of the present claims or through presentation of new claims in this or a related application. Such claims, whether broader, narrower, equal, or different in scope to the original claims, also are regarded as included within the subject matter of the present disclosure.

The invention claimed is:

1. A system comprising:
a lubricant passage comprising a lubricant detection system comprising a particle capturing device arranged between a first sensor and a second sensor, wherein the lubricant detection system is shaped to mate with couplings of an engine and an oil filter: and
a controller with instructions stored on non-transitory memory thereof that when executed enable the controller to adjust engine operating parameters in response to feedback from the first and second sensors, wherein the oil filter is a first oil filter, and wherein the particle capturing device is an second oil filter.

2. The system of claim 1, wherein engine operating parameters adjusted in response to feedback from the first sensor include activating an indicator lamp.

3. The system of claim 1, wherein engine operating parameters adjusted in response to feedback from the second sensor include adjusting one or more of a fuel injection and a spark timing.

4. The system of claim 1, wherein the first sensor and the second sensor are one or more of an induction sensor, an infrared sensor, a laser sensor, and an optical sensor.

5. The system of claim 1, wherein the particle capturing device is a magnet.

6. The system of claim 1, wherein the first sensor is one or more of an infrared sensor, a laser sensor, and an optical sensor, and wherein the second sensor is an induction sensor.

7. A vehicle system comprising:
a lubricant detection device comprising a particle capturing device arranged between a first sensor and a second sensor, the particle capturing device comprising a magnet, wherein the lubricant detection device is arranged between and in face sharing contact with an engine and a filter, and wherein the lubricant detection device comprises couplings shaped to mate with an engine bolt of the engine and a receiving hole of the filter with no intervening devices arranged therebetween: and
a controller with instructions stored on non-transitory memory thereof that when executed enable the controller to:
activate an indicator lamp in response to a particle being sensed by only the first sensor; and
adjust an engine power output in response to the particle being sensed by each of the first and second sensors,
the first sensor and the second sensor are identical, and wherein the first sensor and the second sensor are one or more of an infrared sensor, an optical sensor, and a laser sensor.

8. The vehicle system of claim 7, wherein the engine power output is adjusted via one or more of decreasing a fuel injection amount, decreasing boost, and retarding spark.

9. The vehicle system of claim 7, further comprising an oil change request being signaled in response to the particle being sensed.

10. The vehicle system of claim 9, wherein the oil change request is removed in response to an oil change being completed, the instructions further enabling the controller to determine degradation of a powertrain component in response to a magnetic particle being sensed within a threshold time following the oil change.

11. The vehicle system of claim 10, wherein the instructions further enable the controller to determine the oil change was inferior in response to a non-magnetic particle being sensed within the threshold time following the oil change.

12. A method comprising:
sensing a particle is in an oil flow in response to feedback from a first sensor of an oil detection system;
activating an indicator lamp engine operating parameter in response to the first sensor sensing the particle and a second sensor not sensing the particle, the second sensor arranged downstream of the first sensor relative to a direction of the oil flow, wherein an oil filter is arranged between the first sensor and the second sensor;
adjusting engine operating parameters to decrease a fuel injection amount in response to the first sensor and the second sensor sensing the particle
signaling an oil change request in response to the first sensor sensing the particle and the second sensor not sensing the particle; and
signaling the oil change request and an oil filter replacement request in response to the first sensor and the second sensor sensing the particle;
the first sensor and the second sensor are different, wherein the first sensor is a non-inductive sensor selected from one or more of an infrared sensor, an optical sensor, and a laser sensor, and wherein the second sensor is an inductive sensor.

13. The method of claim 12, wherein the oil flow is flowing from an oil sump to an engine.

14. The method of claim 12, wherein the oil filter is the only oil filter of a vehicle.

\* \* \* \* \*